(12) United States Patent
Errico et al.

(10) Patent No.: US 9,414,932 B2
(45) Date of Patent: Aug. 16, 2016

(54) STAND ALONE ANTERIOR CAGE

(71) Applicant: Stryker European Holdings I, LLC, Kalamazoo, MI (US)

(72) Inventors: Thomas J. Errico, New York, NY (US); Alexandre B. de Moura, Westbury, NY (US); Christopher McDonnell, Sandy Hook, CT (US); Rafail Zubok, Midland Park, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 14/608,457

(22) Filed: Jan. 29, 2015

(65) Prior Publication Data

US 2015/0142119 A1 May 21, 2015

Related U.S. Application Data

(62) Division of application No. 12/387,963, filed on May 8, 2009.

(51) Int. Cl.
*A61F 2/44* (2006.01)
*A61F 2/30* (2006.01)
*A61F 2/46* (2006.01)

(52) U.S. Cl.
CPC .............. *A61F 2/442* (2013.01); *A61F 2/4455* (2013.01); *A61F 2002/30504* (2013.01); *A61F 2002/30571* (2013.01); *A61F 2002/30596* (2013.01); *A61F 2002/30598* (2013.01); *A61F 2002/30616* (2013.01); *A61F 2002/30626* (2013.01); *A61F 2002/30632* (2013.01); *A61F 2002/30736* (2013.01); *A61F 2002/30787* (2013.01); *A61F 2002/30843* (2013.01); *A61F 2002/30848* (2013.01); *A61F 2002/4475* (2013.01); *A61F 2002/4629* (2013.01); *A61F 2220/0025* (2013.01); *A61F 2310/00017* (2013.01); *A61F 2310/00023* (2013.01)

(58) Field of Classification Search
CPC ..... A61F 2/442; A61F 2/4425; A61F 2/4455; A61F 2/447; A61F 2/4475; A61F 2002/443; A61F 2002/4475
USPC ...................... 623/17.11, 17.12, 17.15, 17.16
See application file for complete search history.

(56) References Cited

U.S. PATENT DOCUMENTS

| 5,645,599 | A  | 7/1997  | Samani        |
| 5,782,832 | A  | 7/1998  | Larsen et al. |
| 6,102,950 | A  | 8/2000  | Vaccaro       |
| 6,436,140 | B1 | 8/2002  | Liu et al.    |
| 6,443,989 | B1 | 9/2002  | Jackson       |
| 6,648,917 | B2 | 11/2003 | Gerbec et al. |
| 6,709,458 | B2 | 3/2004  | Michelson     |
| 6,773,460 | B2 | 8/2004  | Jackson       |
| 6,821,298 | B1 | 11/2004 | Jackson       |
| 6,835,206 | B2 | 12/2004 | Jackson       |

(Continued)

*Primary Examiner* — Nicholas Plionis
(74) *Attorney, Agent, or Firm* — Lerner, David, Littenberg, Krumholz & Mentlik, LLP

(57) ABSTRACT

The present invention teaches an improved spinal fusion implant and method of implanting same. The implant includes a shell and an insert, the insert capable of situating first and second plates of the shell with respect to each other and of preventing unwanted loosening of fasteners placed through the shell and into the adjacent vertebral bodies. The method includes implanting a shell, selecting an insert from a plurality of inserts, and placing an insert between first and second plates of the shell.

20 Claims, 19 Drawing Sheets

(56) References Cited

U.S. PATENT DOCUMENTS

| | | |
|---|---|---|
| 6,989,032 B2 | 1/2006 | Errico et al. |
| 7,008,427 B2 | 3/2006 | Sevrain |
| 7,169,182 B2 | 1/2007 | Errico et al. |
| 2002/0138146 A1* | 9/2002 | Jackson ............... 623/17.15 |
| 2004/0006343 A1 | 1/2004 | Sevrain |
| 2004/0068318 A1 | 4/2004 | Coates et al. |
| 2005/0033433 A1 | 2/2005 | Michelson |
| 2005/0060037 A1 | 3/2005 | Michelson |
| 2005/0113916 A1 | 5/2005 | Branch |
| 2006/0085071 A1 | 4/2006 | Lechmann et al. |
| 2006/0149377 A1 | 7/2006 | Navarro et al. |
| 2006/0167547 A1 | 7/2006 | Suddaby |
| 2007/0191953 A1 | 8/2007 | Trieu |
| 2007/0225806 A1 | 9/2007 | Squires et al. |

* cited by examiner

STAND ALONE ANTERIOR CAGE

CROSS-REFERENCE TO RELATED APPLICATIONS

This application is a divisional of U.S. application Ser. No. 12/387,963 filed May 8, 2009, the disclosure of which is incorporated herein by reference.

BACKGROUND OF THE INVENTION

The present invention is directed to spinal implants, and more particularly, spinal fusion implants.

The deterioration of vertebral bodies and/or vertebral discs is a major cause of back and neck pain in many patients. Through the years, many different techniques for restoring the natural anatomical spacing in the spine and thereby alleviating this pain have been developed and practiced by surgeons. For instance, implants and techniques for implanting such implants have been designed to preserve motion between adjacent vertebral bodies. These motion preserving implants are adapted to emulate a removed spinal disc. Examples of such implants (and the methods of implanting same) are disclosed in U.S. Pat. No. 6,989,032 ("the '032 patent") and U.S. Pat. No. 7,169,182 ("the '182 patent"), the disclosures of which are hereby incorporated by reference herein. Nonetheless, even given the success of such motion preserving devices, it is still sometimes necessary to fuse adjacent vertebral bodies so that no movement is permitted therebetween.

Spinal fusion surgery typically involves removing the disc material from between adjacent vertebral bodies, which thereby creates an empty intervertebral space. In this space is implanted an implant or cage that is then fixably mounted to the end plates of the adjacent vertebral bodies. Bone growth is often permitted through the implant, and is in fact sometimes provoked by the placement of bone growth inducing substances within the cage. However, even given this bone growth through the cage, it is sometimes necessary to at least initially mount the cage to the vertebral bodies through the use of fixation elements such as screws. Furthermore, it has also determined that providing an angled implant or cage can aid in returning the adjacent vertebral bodies to their natural "lordotic" angle.

Even if a surgeon initially determines that he or she wishes to perform a motion preserving surgery on a patient, sometimes it becomes apparent during the procedure that a fusion procedure would benefit the patient. Likewise, surgeons often recognize the need to fuse vertebral bodies at levels adjacent to the initial one in question. Thus, it is desirable to have a fusion implant that can easily be implemented and implanted utilizing the tools and procedure used in a motion preserving surgery. Moreover, it is also desired to have such a fusion implant be easily implanted using those tools, easily affixed to the intervertebral bodies, and prevented from becoming dislodged even after just initially being implanted.

Therefore, there exists a need for an improved spinal fusion device.

SUMMARY OF THE INVENTION

A first aspect of the present invention is a spinal implant for fusing together first and second vertebral bodies. In accordance with one embodiment of this first aspect, the implant includes a first member having a first surface for engaging the first vertebral body, a second surface, and a first opening extending between the first and second surfaces. The implant also includes a second member having a third surface for engaging the second vertebral body, a fourth surface, and a second opening extending between the third and fourth surfaces. A living hinge connecting the first and second members is also included and preferably allows for movement of the first and second members with respect to one another. Finally, an insert is disposed between the first and second members, the insert covering the first and second openings about the second and fourth surfaces.

In accordance with other embodiments of the first aspect, the second and fourth surfaces may include a projection for retaining the insert between the first and second members, and in other embodiments each of the second and fourth surfaces include these projections. The insert may be constructed of bone, polymer, metal, or the like. Furthermore, the implant may include a first screw disposed in a first opening and a second screw disposed in a second opening, and the insert may include a portion for preventing backout of the first and second screws. In still further embodiments, the first member may include a third opening extending between the first and second surfaces, and the second member may include a fourth opening extending between the third and fourth surfaces. In this embodiment, the insert may include a main body, a first portion for covering the first and second openings, and a second portion for covering the third and fourth openings. The insert may also include an aperture for engagement with a tool. In accordance with this further embodiment, a first screw may be disposed in the first opening, a second screw may be disposed in a second opening, a third screw may be disposed in the third opening, and a fourth screw may be disposed in the fourth opening. The insert includes a first portion for preventing backout of the first and second screws and a second portion for preventing backout of the third and fourth screws. Finally, in accordance with certain embodiments, the implant may include a bone growth aperture extending through the first member, the insert, and the second member, and the implant may be designed to provide a nonparallel relationship between the first and second surfaces, such that the vertebral bodies exhibit a similar relationship.

The second aspect of the present invention is also directed to a spinal implant for implantation between first and second vertebral bodies. In accordance with one embodiment of this second aspect, the implant includes a shell and an insert. The shell preferably includes a first plate for engaging the first vertebral body, the first plate including a first hole formed therethrough, a second plate for engaging the second vertebral body, the second plate including a second hole formed therethrough, and a resilient member connecting the first and second plates. The insert on the other hand may include a main body and a portion capable of covering at least one of the first or second holes when the insert is disposed between the first and second plates.

In accordance with other embodiments of the second aspect, the implant may include a first screw disposed in the first hole, and a second screw disposed in the second hole. A portion of the insert is preferably capable of preventing backout of both of the first and second screws when the insert is disposed between the first and second plates. The insert may be constructed at least partially from materials selected from the group consisting of bone, polymer, and metal. At least one of the first and second plates may include a projection for retaining the insert between the first and second plates, but in certain embodiments both the first and second plates may include such projections. The implant may also include a third hole formed through the first plate and a fourth formed through the second plate, and a first screw disposed in the first hole, a second screw disposed in the second hole, a third screw disposed in the third hole, and a fourth screw disposed in the fourth hole. The insert may include a first portion for preventing backout of the first and second screws and a second portion for preventing backout of the third and fourth screws. A bone growth aperture may extend through the first member, the insert, and the second member. The insert may include an aperture for engagement with the tool. Preferably, the first and second plates are located in nonparallel planes, and such may be caused by the insert being placed therebetween.

The third aspect of the present invention is a method of fusing together first and second vertebral bodies. In accordance with one embodiment of the present invention, the method includes the steps of preparing a space between the first and second vertebral bodies to a spinal implant, implanting a shell, the shell including a first plate, a second plate, and a living hinge connecting the first and second plates, placing a first screw through the first plate and into the first vertebral body, placing a second screw through the second plate and into the second vertebral body, and inserting an insert between the first and second plates, wherein the insert prevents backout of the first and second screws.

In accordance with other embodiments of this third aspect, the inserting step may cause the first and second plates to move with respect to each other and such movement between the first and second plates is preferably translated to the first and second vertebral bodies. The method may also include the step of choosing an insert from a plurality of inserts. Moreover, the method may include the step of placing a third screw through the first plate and into the first vertebral body, and the step of placing a fourth screw through the second plate in the intervertebral body. Preferably, the insert prevents backout of the first, second, third, and fourth screws. The method may also include the step of retaining the insert between the first and second plates, where this retaining step may include engaging the insert with projections formed on the first and second plates. Finally, the method may also include the step of allowing bone growth through an aperture formed through the first plate, the insert, and the second plate.

BRIEF DESCRIPTION OF THE DRAWINGS

A more complete appreciation of the subject matter of the present invention and the various advantages thereof can be realized by reference to the following detailed description with reference to the accompanying drawings in which.

DETAILED DESCRIPTION

Figure 1:
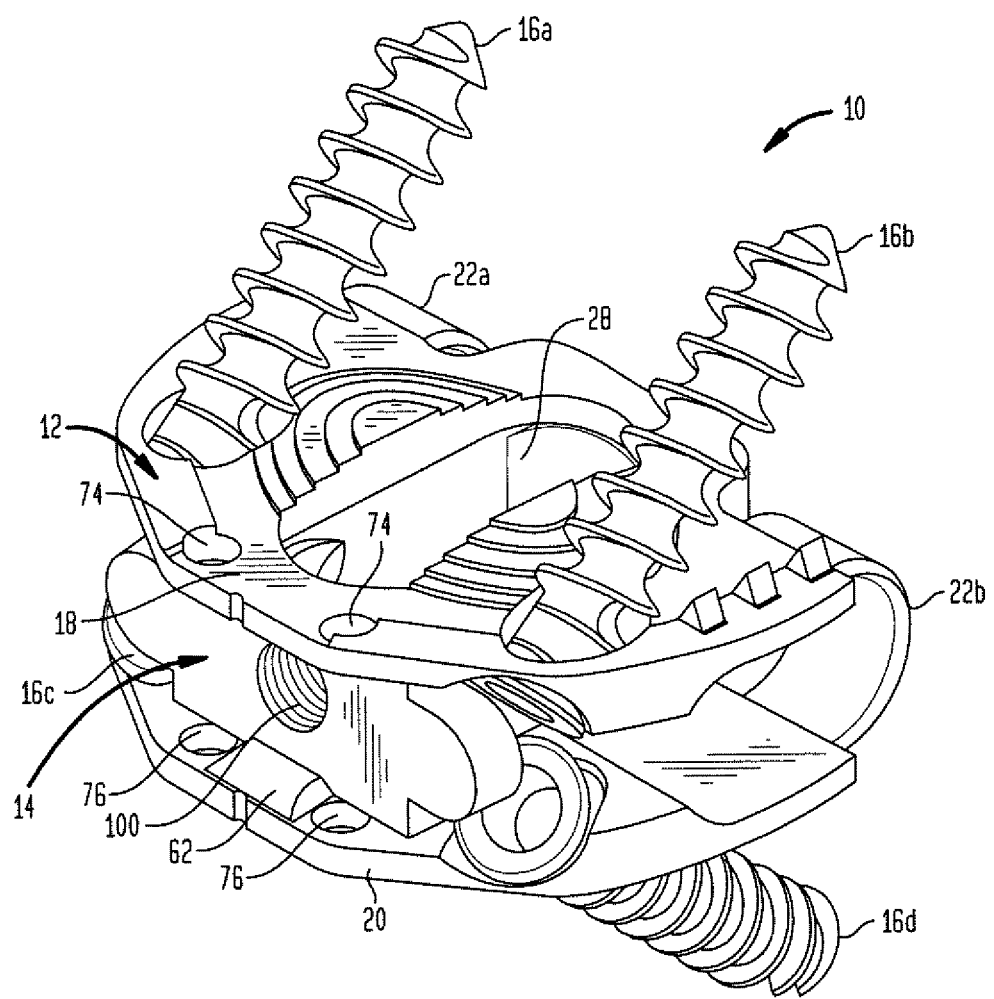
FIG. 1 is a perspective view of an intervertebral fusion implant according to one embodiment of the present invention.
Figure 2:
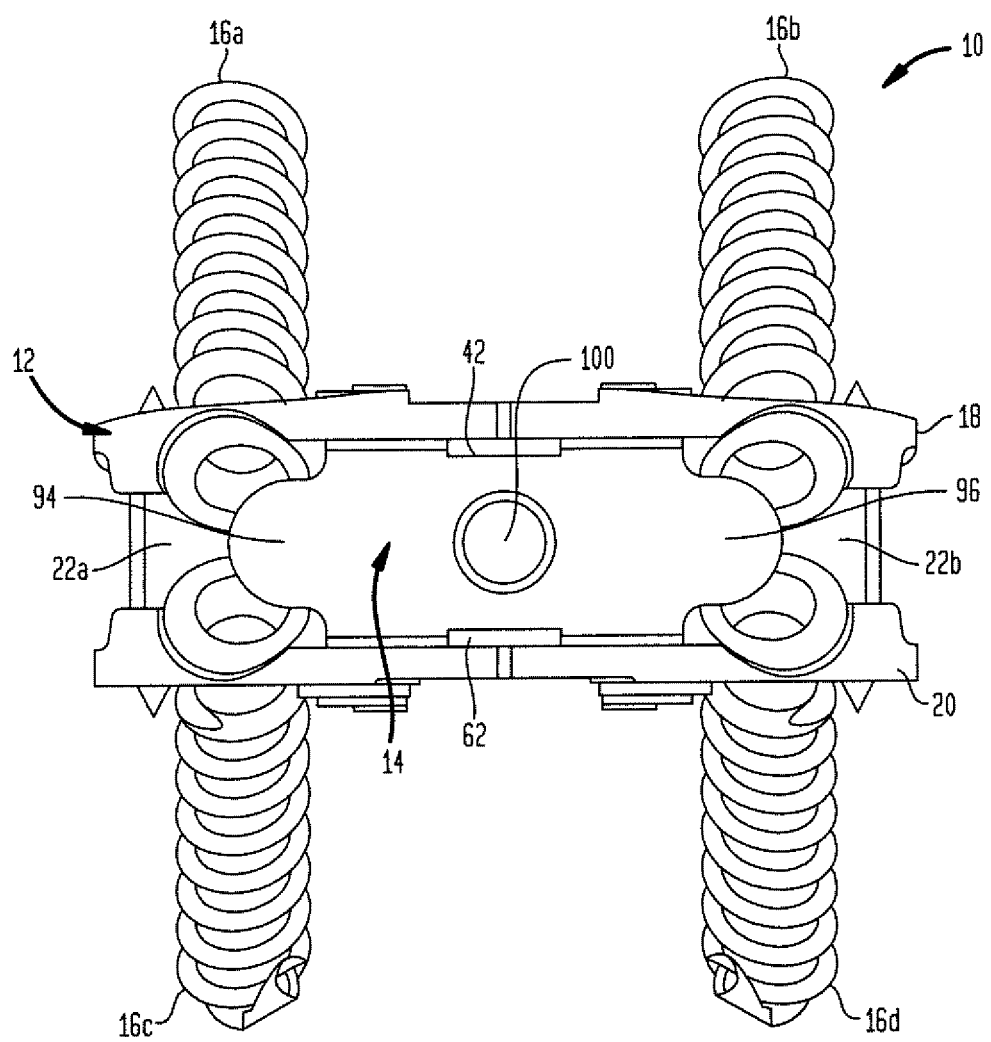
FIG. 2 is a front view of the implant shown in FIG. 1.
Figure 3:
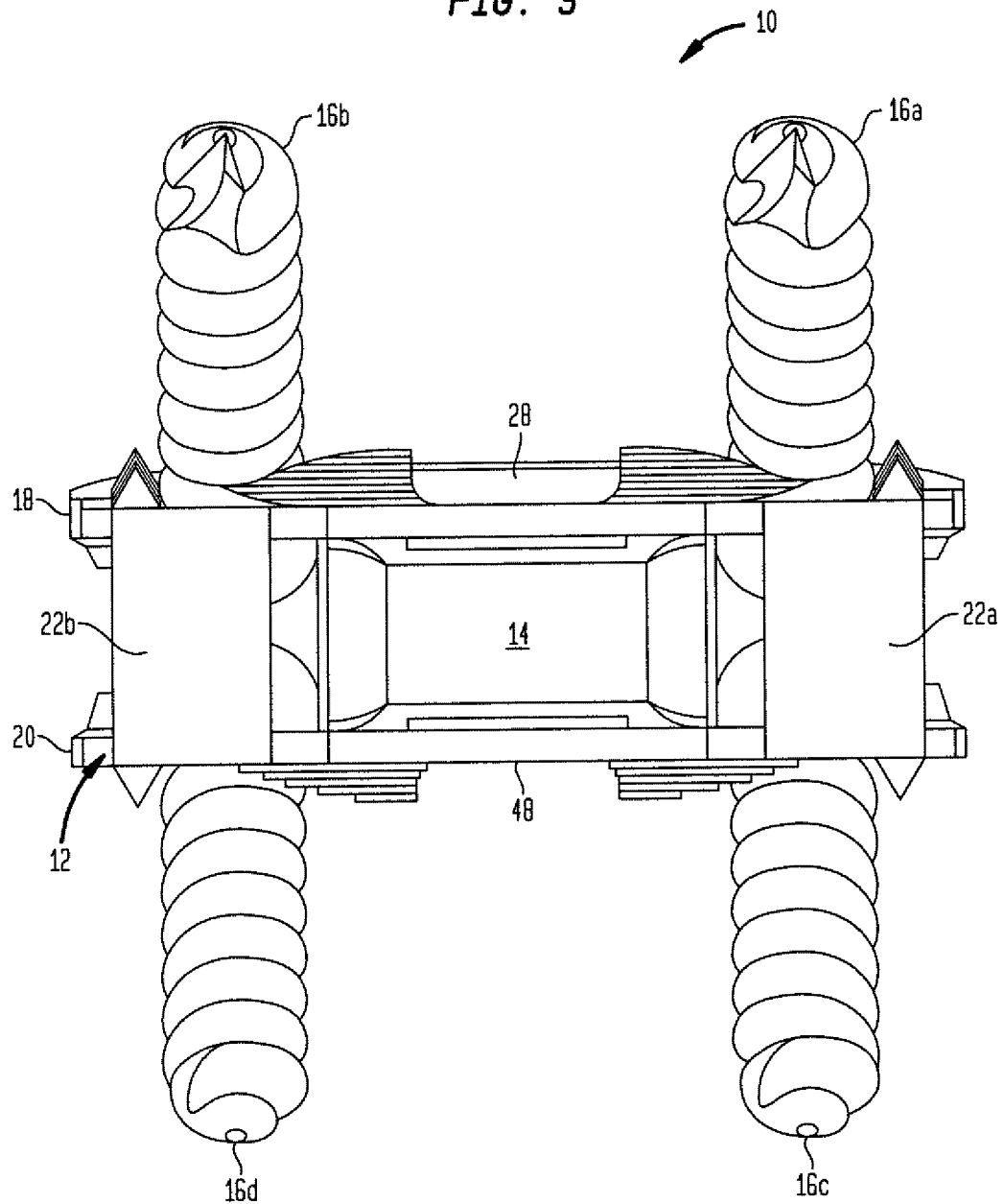
FIG. 3 is a rear view of the implant shown in FIG. 1.
Figure 4:
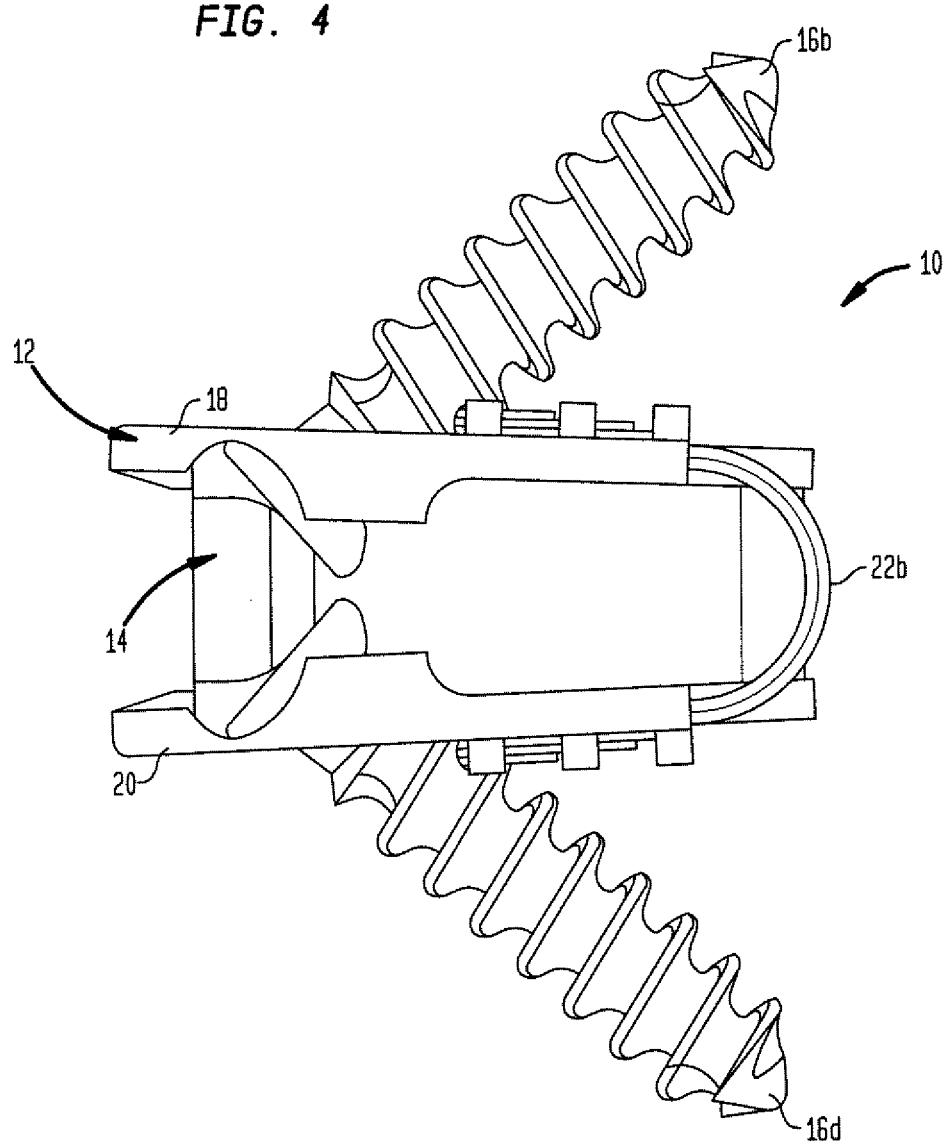
FIG. 4 is a right side view of the implant shown in FIG. 1.
Figure 5:
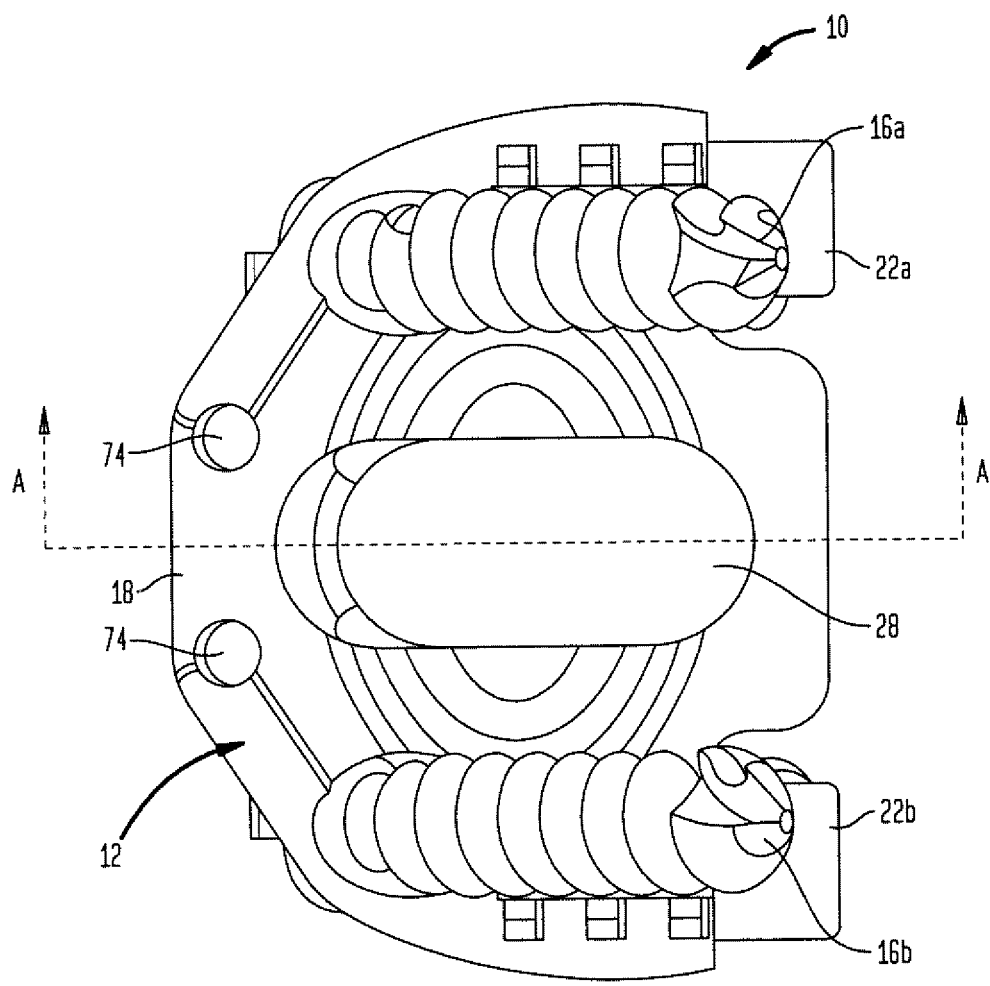
FIG. 5 is a top view of the implant shown in FIG. 1.
Figure 6:
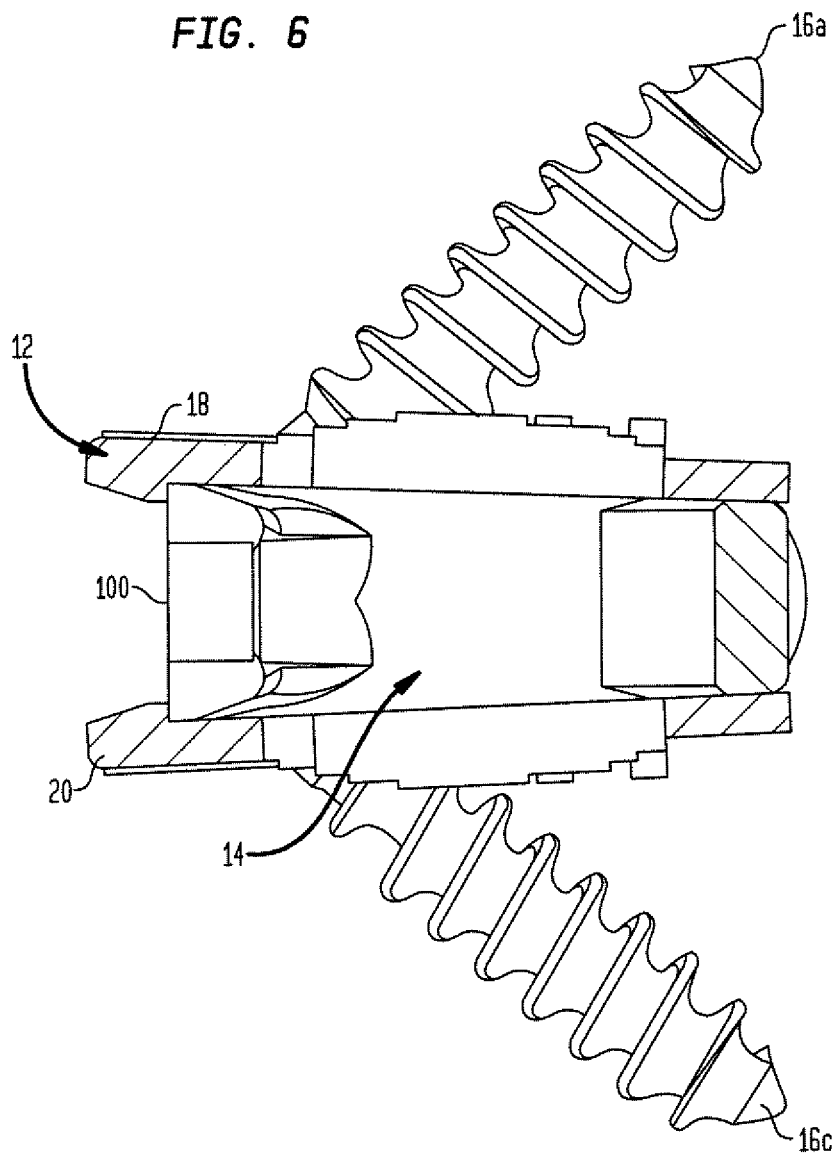
FIG. 6 is a cross-sectional view of the implant shown in FIG. 1 taken along line A-A of FIG. 5.

Referring to the drawings, wherein like reference numerals refer to like elements, FIGS. 1-6 depict a first embodiment intervertebral fusion device or spinal implant for fusing together first and second vertebral bodies, designated generally by reference numeral 10. As is shown in the drawings, implant 10 includes a shell 12 and an insert 14. Moreover, implant 10 is also provided with a plurality of fasteners (shown in the drawings as screws 16a-d) for placement through portions of the shell and into adjacent vertebral bodies. However, one of ordinary skill in the art would readily recognize that other types of fasteners could be utilized, e.g., pins or the like. The specifics of each of the components of implant 10, as well as their operation and use will be discussed more fully below.

Figure 7:
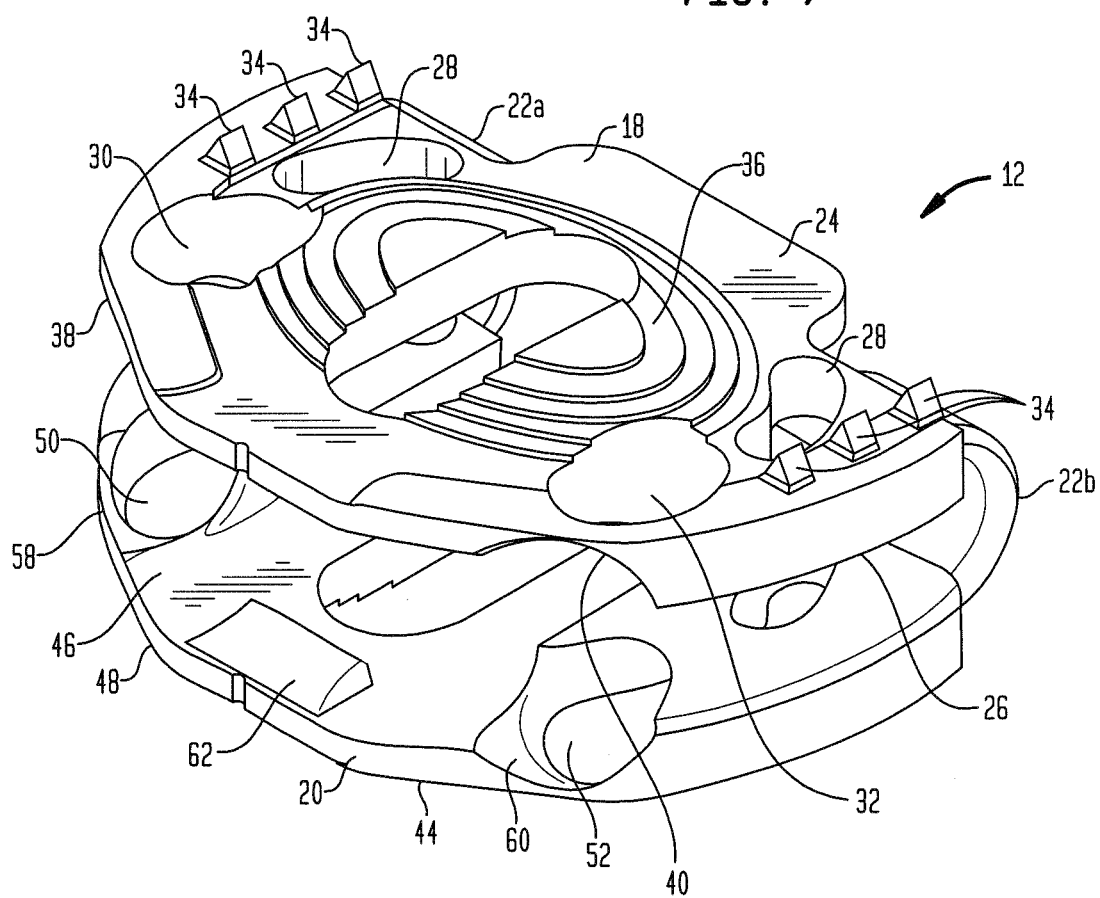
FIG. 7 is a perspective view of a shell from the implant of FIG. 1.
Figure 8:
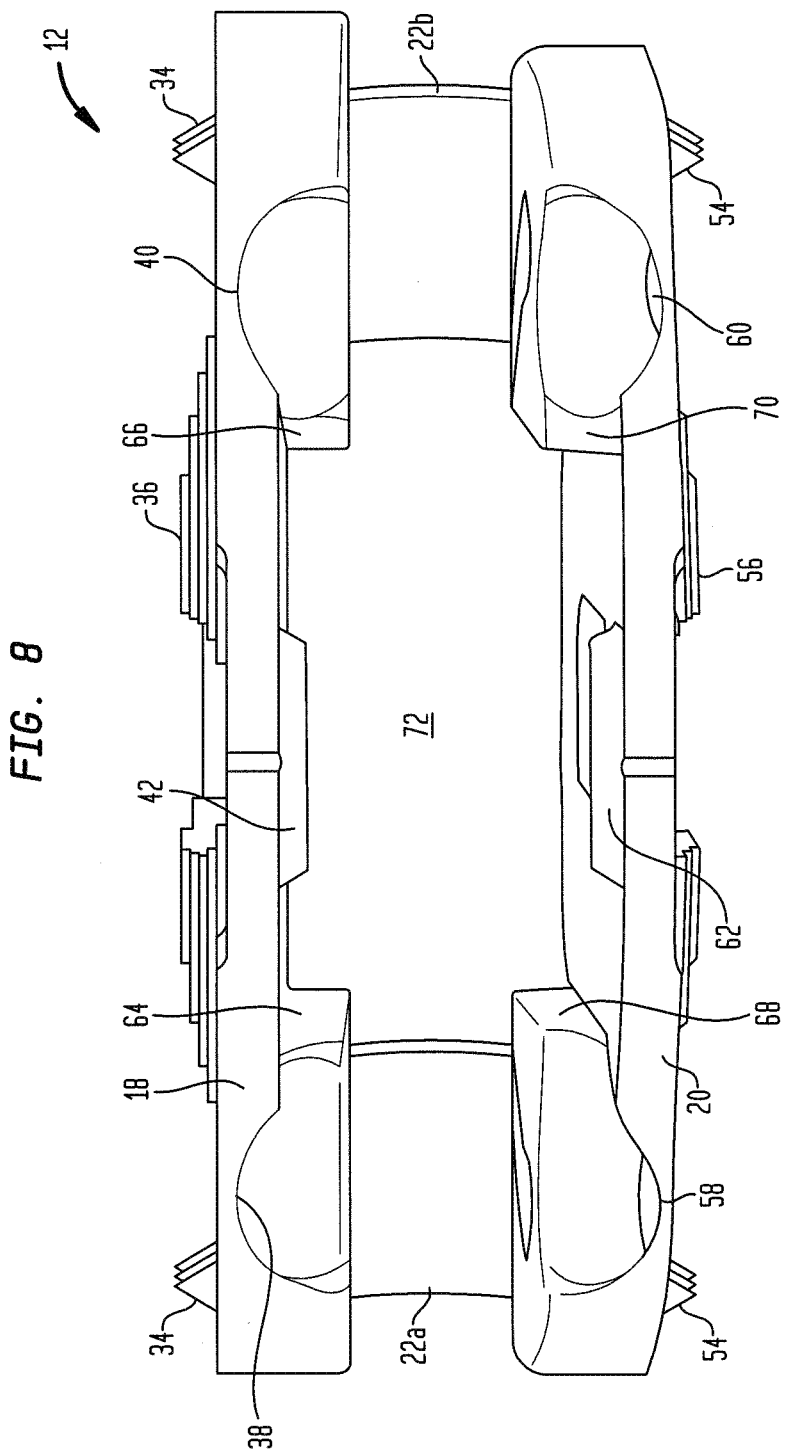
FIG. 8 is a front view of the shell shown in FIG. 7.
Figure 9:
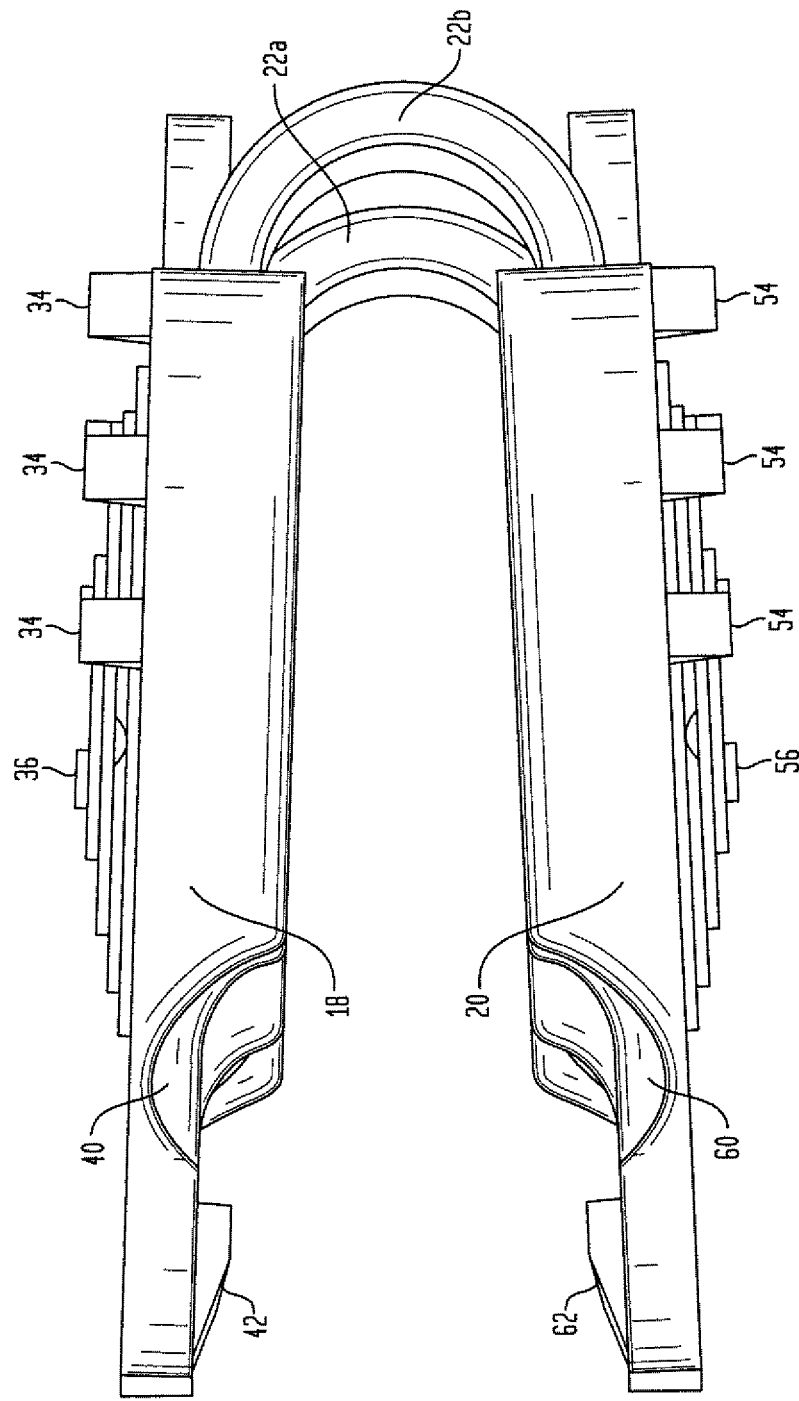
FIG. 9 is a right side view of the shell shown in FIG. 7.
Figure 10:
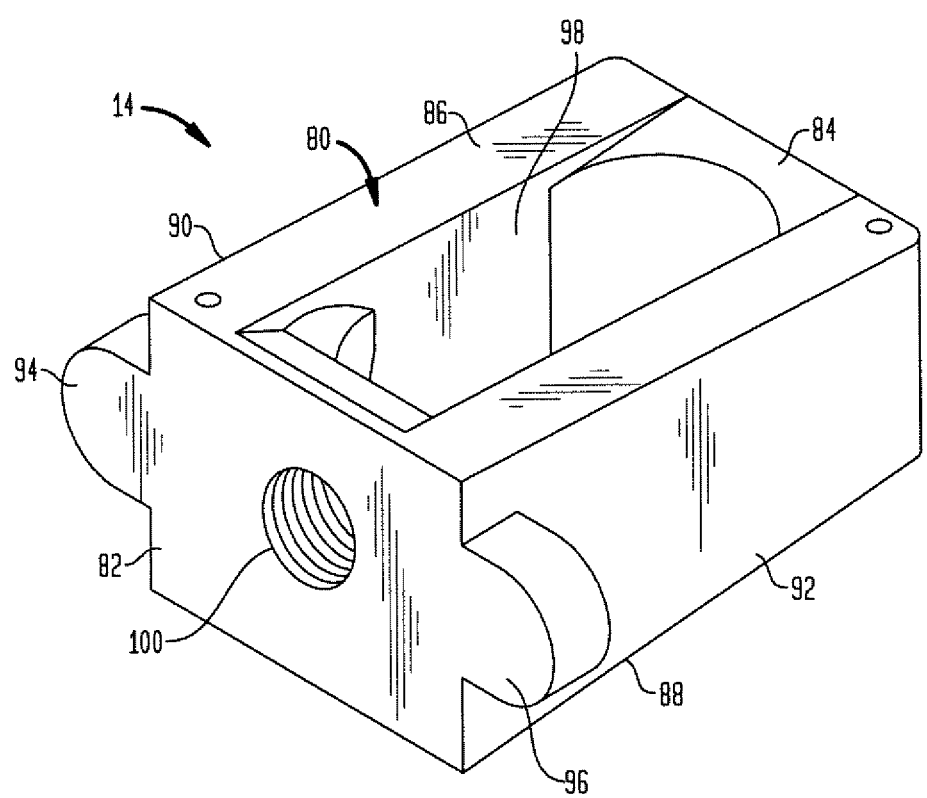
FIG. 10 is a perspective view of an insert from the implant shown in FIG. 1.
Figure 11:
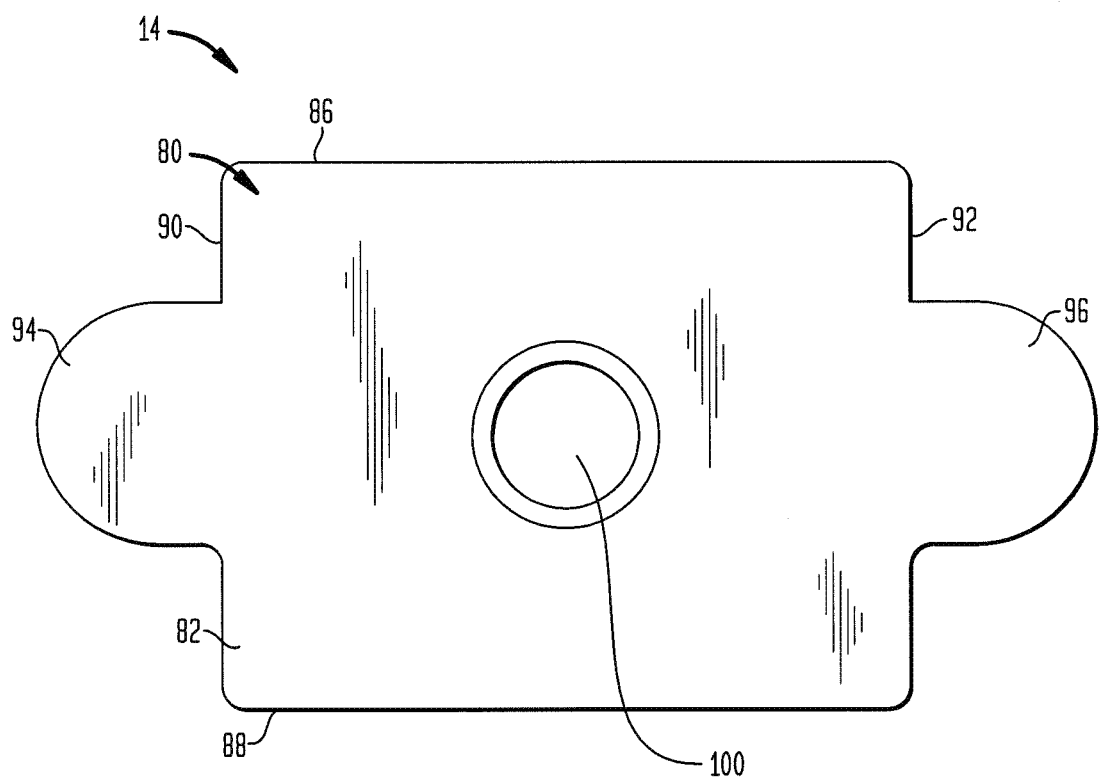
FIG. 11 is a front view of the insert shown in FIG. 10.
Figure 12:
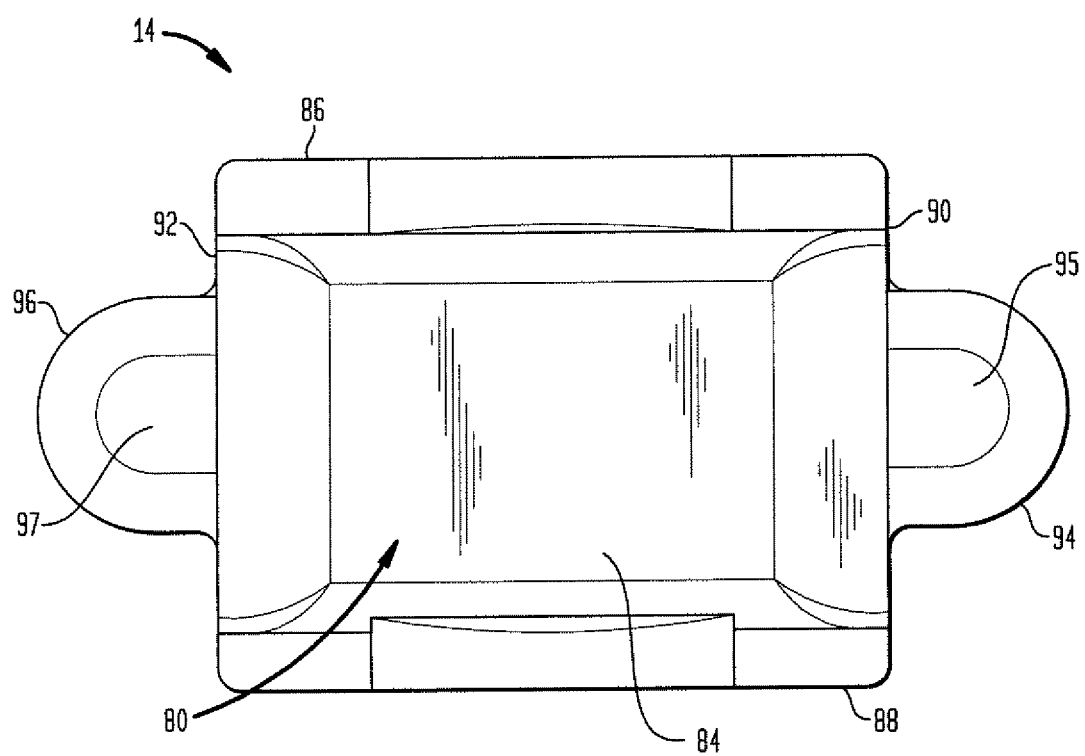
FIG. 12 is a rear view of the insert shown in FIG. 10.
Figure 13:
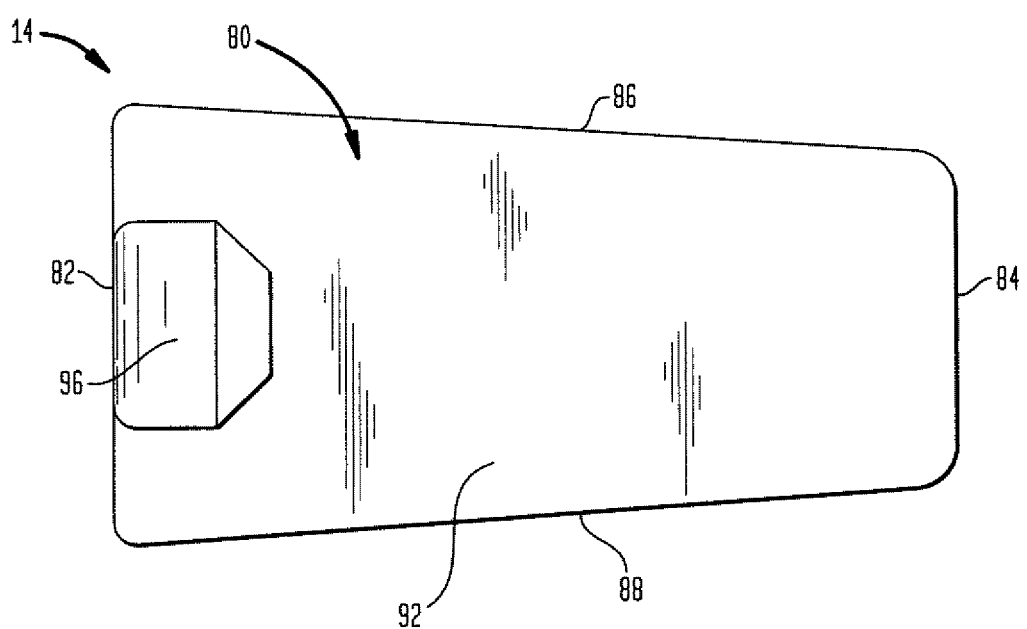
FIG. 13 is a right side view of the insert shown in FIG. 10.
Figure 14:
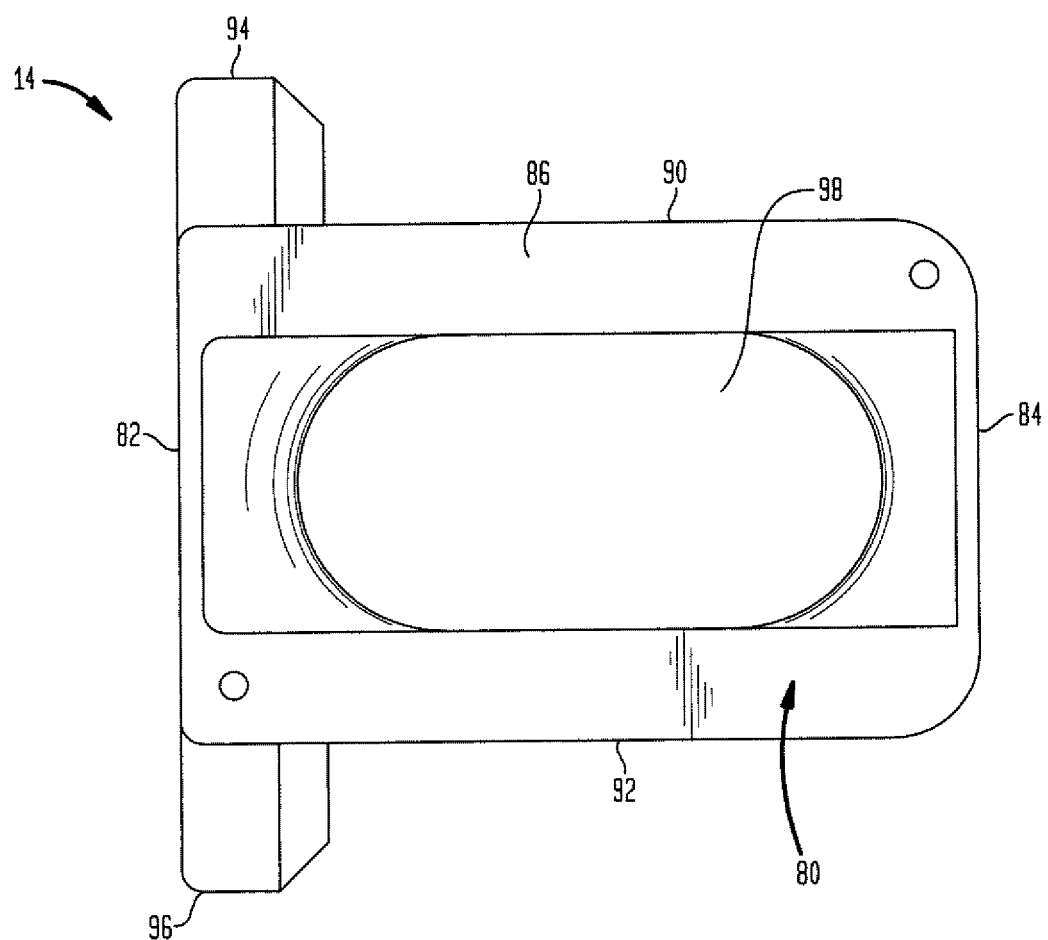
FIG. 14 is a top view of the insert shown in FIG. 10.

As is shown in FIGS. 1-6 and even more specifically shown in FIGS. 7-9, shell 12 includes a first plate or member 18, a second plate or member 20, and a pair of resilient or living hinge members 22a and 22b. First member 18 includes a first surface 24 for engaging an upper vertebral body, a second surface 26 for engagement with insert 14, a plurality of bone growth apertures collectively referred to by reference numeral 28, and two fastener holes 30 and 32. First surface 18 is formed with a plurality of vertebral body engaging members, including teeth 34 and surfaces 36. Second surface 26 is formed with countersunk surfaces 38 and 40 in the vicinity of fastener holes 30 and 32, respectively, and a projection 42 extending toward second member 20. Similarly, second member 20 includes a third surface 44 for engagement with the lower vertebral body, a fourth surface 46 for engagement with insert 14, a plurality of bone growth apertures collectively referred to with reference numeral 48, and two fastener holes 50 and 52. Also in a similar fashion to first member 18, third surface 44 is formed with vertebral engaging elements including teeth 54 and surfaces 56, while second surface 46 includes countersinks 58 and 60 in the vicinity of fastener holes 50 and 52, respectively, and projection 62 extending toward first 18. Moreover, as is best shown in FIG. 8, extending from second surface 26 of first member 18 are extensions 64 and 66, and extending from fourth surface 46 of second member 20 are extensions 68 and 70. These extensions create a substantially rectangular space 72 for reception of insert 14, as will be discussed more fully below. First plate 18 may also include apertures 74 and second plate 20 may include apertures 76, which are utilized in engaging an insertion tool.

Resilient members 22a and 22b are shown as living hinges. Essentially, these elements are curved elements being made of a material capable of bending upon an application of force to one of or both of first and second members 18 and 20. For example, upon placement of differently sized inserts 14 between the first and second members, hinges 22a and 22b are capable of allowing for the expansion or the contraction of the device. While shown in the drawings as being composed of the same material as first and second members 18 and 20, it is noted that members 22a and 22b can be constructed of different materials. Likewise, the overall shape of members 22a and 22b can vary from the rounded structures shown in the drawings.

In the embodiment shown in the drawings, shell 12 is formed of titanium, but it is noted that other materials such as stainless steel, polymer, or the like can be utilized. It is also noted that the specific configuration of shell 12 may widely vary in different embodiments of the present invention. For example, the overall shape of the shell which is shown as being similar in nature to the implants shown and described in the '032 and '182 patents, but may vary depending upon the different portion of the spine in which it is to be implanted or the design of an implant of which it is to emulate. The vertebral engaging surfaces may also vary, including the specific vertebral engaging members disposed thereon. Furthermore, the apertures extending through the first and second members may vary, including the overall amount of bone growth apertures and screw holes. While fastener holes 30, 32, 50, and 52 are shown as being angled, other angles and/or perpendicular configurations are contemplated. Likewise, the configuration of projections 42 and 62 may also vary as can the space 72 for accepting insert 14.

Turning now to the configuration of insert 14, it is noted that such is preferably of a unitary construction. However, in other embodiments, different configurations are contemplated. With specific reference to FIGS. 10-14, insert 14 includes a main body 80 having a front face 82, a rear face 84, a top surface 86, a bottom surface 88, a left side surface 90, and a right side surface 92. Extending from the left and right are flanges 94 and 96, such that they form a continuous surface with front face 82, flange 94 includes a rear face 95, and flange 96 includes a rear face 97. In addition, as is shown in the drawings, formed through top surface and bottom surface is an aperture 98, which generally cooperates with apertures 28 and 48 of first and second members 18 and 20, respectively, in order to provide for a bone growth channel between adjacent vertebral bodies. Finally, front face includes an aperture 100, which is shown as being threaded for engagement with an insertion tool (not shown).

It is to be understood that insert 14 may widely vary from that which is shown in the drawings. For one, insert 14 may vary to properly cooperate with variations of shell 12. Certain portions of insert 14 may also vary and still be capable of cooperating with shell 12 as shown. For instance, flanges 94 and 96 may simply be extensions of front face 82 (i.e., rectangular) rather than the rounded structures that are illustrated in the drawings. Moreover, aperture 100 may be configured differently to engage an insertion tool (not shown). For instance, insert 14 may include an aperture 100 which is meant to cooperate with a spring detent or the like. Additionally, insert 14 may include a differently configured aperture 98 (or multiple apertures) for cooperation with like apertures formed in first and second members 18 and 20 of shell 12. Finally, insert 14 may be constructed of many different types of materials. For example, it is contemplated to form insert 14 of PEEK™ or of a biological material such as bone. In the case of the latter, the patient's own bone may be utilized to form insert 14 by any one of many known processes.

Figure 15:
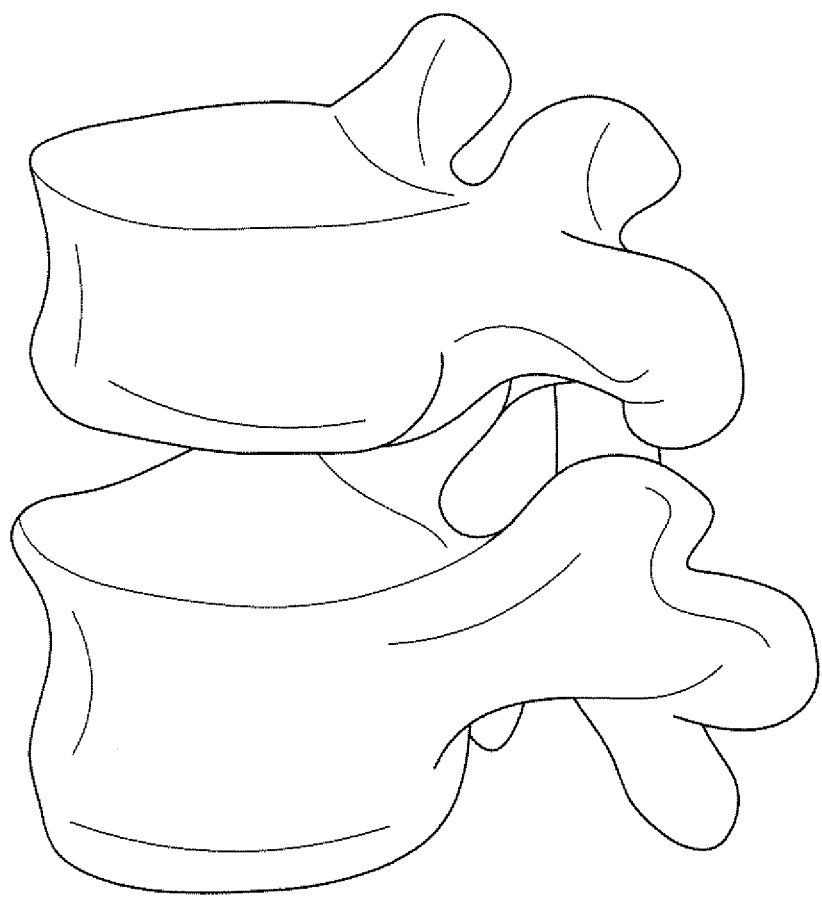
FIG. 15 is a prospective view of adjacent vertebral bodies having been prepared to receive a fusion implant.
Figure 16:
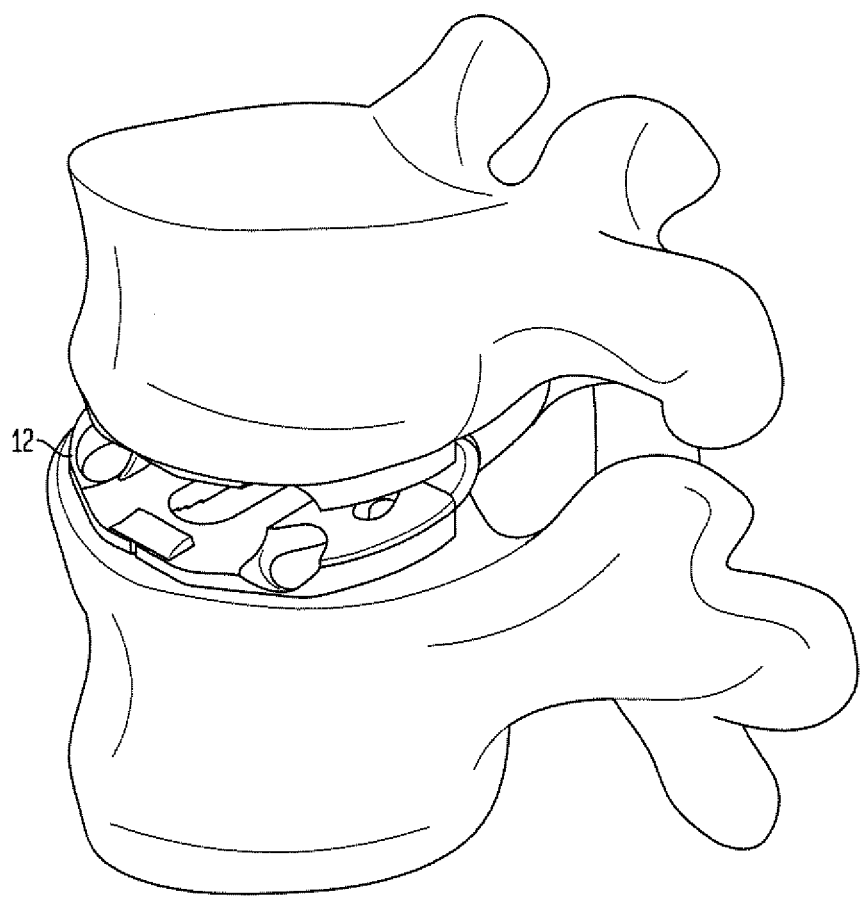
FIG. 16 is a prospective view of the vertebral bodies of FIG. 15 having the shell shown in FIG. 7 implanted therebetween.
Figure 17:
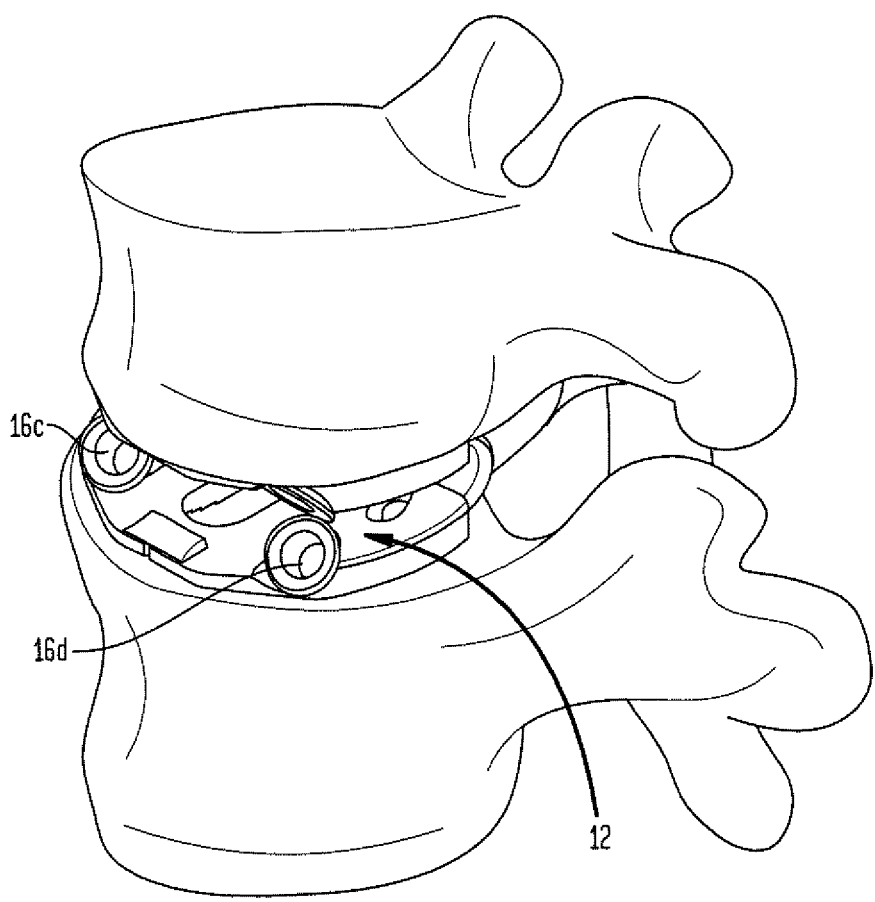
FIG. 17 is a prospective view similar to the one shown in FIG. 16 with screws implanted through the shell and into the adjacent vertebral bodies.

During a surgical procedure in which the above-discussed implant 10 is implanted, the surgeon first sees to the preparation of the intervertebral space between the adjacent vertebral bodies in order to be capable of receiving shell 12. This is shown in FIG. 15 and may include the removal of disc material and/or the preparation of the end plates of the vertebral bodies. Shell 12 is then inserted in the prepared space (see FIG. 16). In this regard, an insertion tool (not shown) may be engaged with apertures 74 and/or 76 of the first or second plates, or shell 12 may simply be placed by hand into the space. The above-discussed features of surfaces 24 and 44 (i.e., spikes 34 and surfaces 36) may aid in the retainment of shell 12 between the adjacent vertebral bodies. Once in place, fasteners (such as screws 16a-16d shown in FIGS. 1-6) may be placed through fastener holes 30, 32, 50, and 52 and into the adjacent vertebral bodies (see FIG. 17). Once again, it is noted that fastener holes 30, 32, 50, and 52 may be angled in any fashion to allow for specific placement of the fasteners through shell 12 and into the intervertebral bodies. It is noted that although the fasteners are shown in FIGS. 1-6 as screws having specific configurations, many different fastener configurations may be employed in fixing shell 12 to adjacent vertebral bodies, including differently configured screws.

Figure 18:
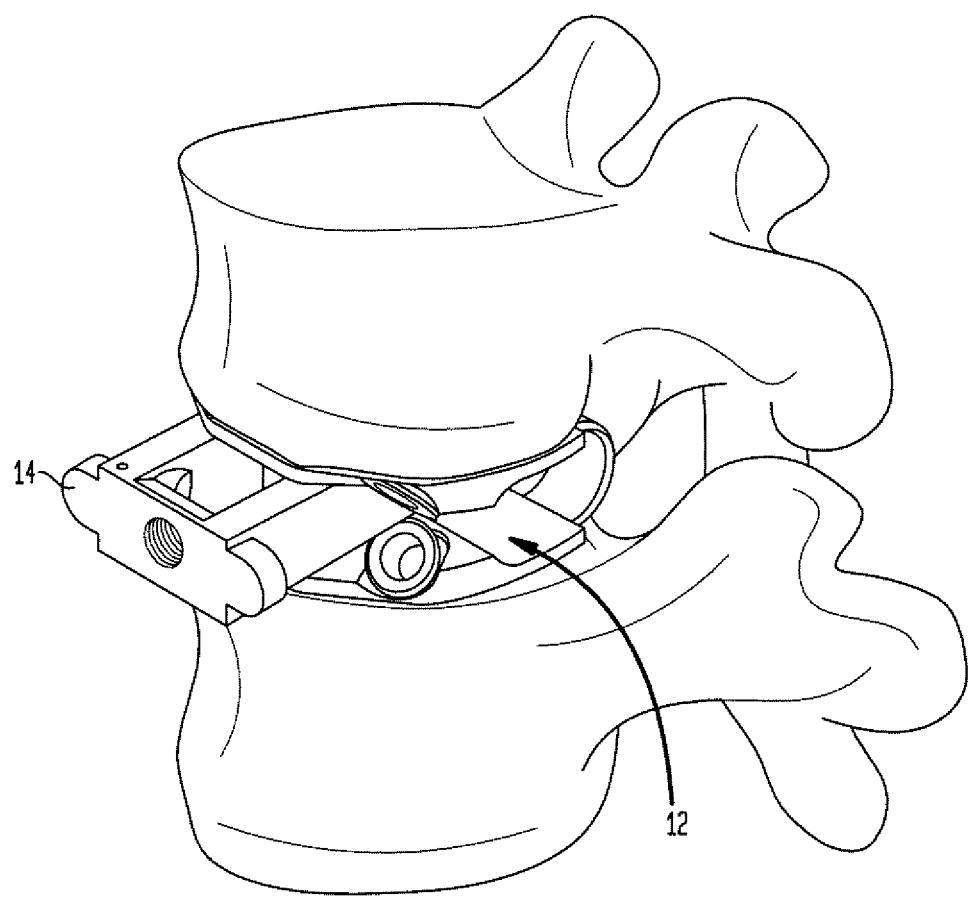
FIG. 18 is a view similar to that of FIG. 17 with the insert of FIG. 10 partially implanted.

With shell 12 in place, insert 14 may then be placed between first and second plates 18 and 20, preferably into above-discussed space 72. Insert 14 partially inserted into shell 12 is shown in FIG. 18. In placing insert 14, a tool (not shown) may be engaged with the threading of aperture 100, or, in the case of a differently configured aperture, another type of connection. Prior to engaging the insert with the tool, a surgeon may select one insert 14 from a plurality of differently sized and/or shaped inserts. These different inserts ultimately affects the disposition of plates 18 and 20 of shell 12. For example, a larger sized insert would increase the distance between plates 18 and 20, while differently shaped inserts may affect the amount of angle between the plates. Thus, depending upon the spacing or lordotic angle desired between adjacent vertebral bodies, different inserts having different sizes and/or differently angled upper and lower surfaces may be selected.

Figure 19:
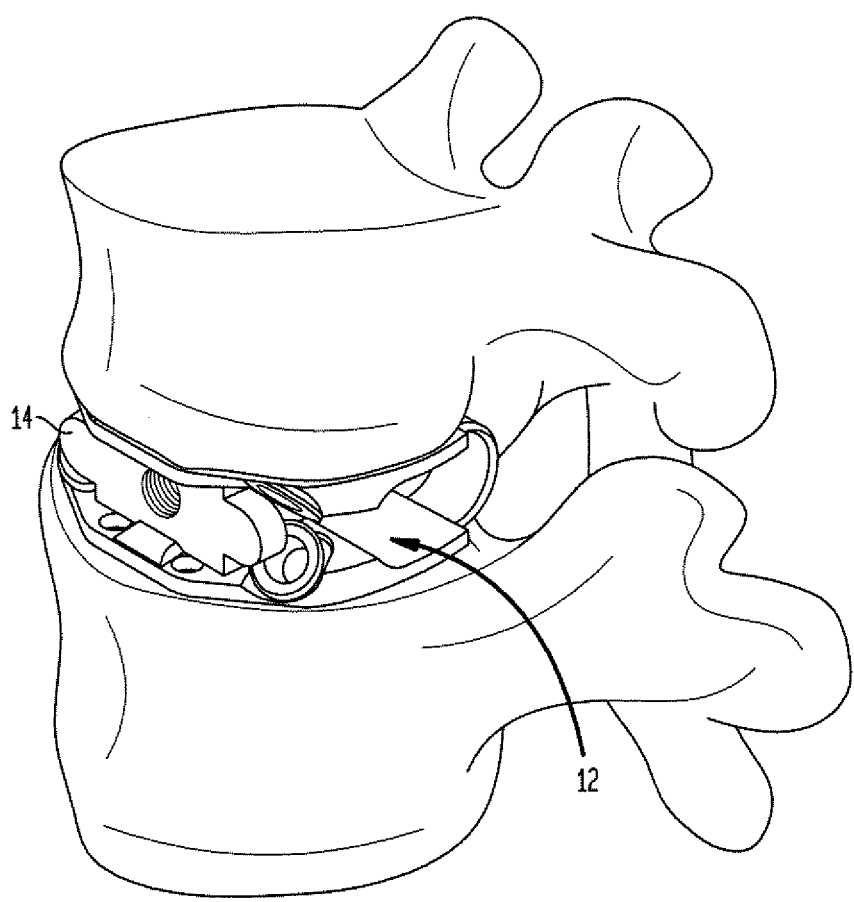
FIG. 19 is a view similar to FIG. 18 with the insert completely implanted.

Once the surgeon makes the proper determination of the insert to utilize, it is coupled with a tool (not shown) or placed by hand between plates 18 and 20 (see FIG. 18). This placement of the insert preferably moves plates 18 and 20, and thusly the adjacent vertebral bodies to the position desired. Living hinges 22a and 22b allow for this movement while at the same time forcing plates 18 and 20 toward insert 14. At a certain point, front face of insert 14 is pushed past projections 42 and 62 so that the insert is forcibly maintained within space 72 of shell 12 (see FIG. 19). In this regard, it is noted that projections 42 and 62 are designed as ramps, which preferably allow for the easy insertion of insert 14 within space 72. However, once front face of insert 14 passes projections 42 and 62, the insert is thereby retained within the space. It is noted that other configurations for projections 42 and 62 may be employed. Once in this position, flanges 94 and 96 of insert 14 are disposed at least partially over a portion of the fasteners placed within fastener holes 30, 32, 50, and 52. In the preferred embodiment shown in the drawings, flanges 94 and 96 are placed over the heads of screws 16a-16d (best shown in FIG. 2). This final position for insert 14 and its projections preferably prevents the loosening or backout of the screws that may occur. In other words, flanges 94 and 96 prevent the screws from coming out of the vertebral bodies.

As is mentioned above, insert 14 may be made of various materials. For example, the insert may be constructed at least partially of metal, polymer, and/or bone material. In the latter case, insert 14 may encourage growth of bone through aperture 28, aperture 98, and aperture 48 to thereby fuse the adjacent vertebral bodies. Furthermore, it is contemplated that bone growth including substances may be placed within these apertures (or one of the apertures) in order to even further facilitate or, in the case of inserts constructed of non-bone material, promote such growth. It is contemplated that other embodiments of shell 12 and insert 14 may include additional apertures which promote further grown from adjacent vertebral bodies therethrough.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of fusing together first and second vertebral bodies, the method comprising:
   preparing a space between the first and second vertebral bodies to accept a spinal implant;
   implanting a shell including,
      a first plate having a first end, a second end, a first length between the first and second ends, and a first aperture,
      a second plate having a third end, a fourth end, a second length between the third and fourth ends, and a second aperture, and
      a living hinge connecting the first and second plates at the second and fourth ends;
   placing a first screw through the first plate and into the first vertebral body;
   placing a second screw through the second plate and into the second vertebral body; and
   after the implanting and placing steps, inserting an insert between the first and second plates such that the insert extends along a majority of the first and second lengths, wherein the insert prevents back out of the first and second screws and the insert includes a third aperture aligned with the first and second apertures.

2. The method of claim 1, wherein the inserting step causes the first and second plates to move with respect to each other, wherein the movement between the first and second plates is translated to the first and second vertebral bodies.

3. The method of claim 1, further comprising the step of choosing the insert from a plurality of inserts.

4. The method of claim 1, further comprising the steps of placing a third screw through the first plate and into the first vertebral body, and placing a fourth screw through the second plate and into the second vertebral body.

5. The method of claim 4, wherein the insert prevents back out of the first, second, third, and fourth screws.

6. The method of claim 5, wherein the insert includes first and second portions and the inserting step includes covering the first and second screws with the first portion and the third and fourth screws with the second portion.

7. The method of claim 1, further comprising the step of retaining the insert between the first and second plates.

8. The method of claim 7, wherein the retaining step includes engaging the insert with projections formed on the first and second plates.

9. The method of claim 1, further comprising the step of allowing bone growth through the first plate, the insert, and the second plate.

10. The method of claim 1, further including the step of engaging a tool to the insert, wherein the inserting step includes manipulating the tool.

11. The method of claim 1, wherein the inserting step causes the first and second plates to move into non-parallel planes.

12. The method of claim 1, wherein the inserting step causes portions of the first and second plates to engage the first and second vertebral bodies, respectively.

13. A spinal surgery method comprising the steps of:
   contacting a first plate with a first vertebral body, the first plate having a first end, a second end, and a first aperture, and contacting a second plate with a second vertebral body, the second plate having a third end, a fourth end, and a second aperture, the first and second plates connected by a living hinge at the second and fourth ends;
   placing a first fixation element through the first plate in a first direction and into the first vertebral body, the first plate having a first length between the first and second ends;
   placing a second fixation element through the second plate in a second direction and into the second vertebral body, the second plate having a second length between the third and fourth ends;
   engaging an insert with a tool;
   manipulating the tool to insert the insert between the first and second plates such that the insert extends along a majority of the first and second lengths, wherein the insert prevents movement of the first fixation element in a direction opposite to the first direction and the second fixation element in a direction opposite the second direction, and the insert includes a third aperture aligned with the first and second apertures.

14. The method of claim 13, wherein insertion of the insert causes the first and second plates to move with respect to each other.

15. The method of claim 13, further comprising the steps of placing a third fixation element through the first plate and into the first vertebral body, and placing a fourth fixation element through the second plate and into the second vertebral body.

16. The method of claim 15, wherein the insert includes first and second portions and insertion of the insert includes covering the first and second fixation elements with the first portion and the third and fourth fixation elements with the second portion.

17. The method of claim 13, further comprising the step of engaging the insert with projections formed on the first and second plates.

18. The method of claim 13, wherein the placing steps include rotating the first and second fixation elements.

19. The method of claim 13, further comprising the step of allowing bone growth through the first plate, the insert, and the second plate.

20. A spinal surgery method comprising the steps of:
   contacting a first plate having a first end, a second end, a first length between the first and second ends, and a first aperture with a first vertebral body, and contacting a second plate having a third end, a fourth end, and a second length between the third and fourth ends, and a second aperture with a second vertebral body, the first and second plates connected by a living hinge at the second and fourth ends;
   rotating a first screw through the first plate in a first direction and into the first vertebral body;
   rotating a second screw through the second plate in a second direction and into the second vertebral body;
   engaging an insert with a tool;
   manipulating the tool to insert the insert between the first and second plates such that the insert extends along a majority of the first and second lengths, wherein a first portion of the insert prevents movement of the first screw in a direction opposite to the first direction and a second portion of the insert prevents movement of the second screw in a direction opposite the second direction, and the insert includes a third aperture aligned with the first and second apertures.

* * * * *